US010486995B2

(12) United States Patent
Denson, Jr.

(10) Patent No.: US 10,486,995 B2
(45) Date of Patent: *Nov. 26, 2019

(54) SYSTEM AND METHOD FOR CONVERTING ORGANIC WASTE INTO METHANE AND OTHER USEFUL PRODUCTS

(71) Applicant: WM Intellectual Property Holdings, L.L.C., Houston, TX (US)

(72) Inventor: James L. Denson, Jr., Peoria, AZ (US)

(73) Assignee: WM Intellectual Property Holdings, L.L.C., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,021

(22) Filed: Feb. 16, 2017

(65) Prior Publication Data
US 2017/0158539 A1 Jun. 8, 2017

Related U.S. Application Data

(63) Continuation of application No. 14/589,215, filed on Jan. 5, 2015, now abandoned, which is a continuation of application No. 13/169,843, filed on Jun. 27, 2011, now Pat. No. 8,926,841.

(51) Int. Cl.
| | |
|---|---|
| *C02F 11/04* | (2006.01) |
| *B09B 3/00* | (2006.01) |
| *C02F 1/38* | (2006.01) |
| *C02F 3/28* | (2006.01) |
| *C12P 5/02* | (2006.01) |

(52) U.S. Cl.
CPC ........... *C02F 11/04* (2013.01); *B09B 3/00* (2013.01); *C02F 1/385* (2013.01); *C02F 3/28* (2013.01); *C12P 5/023* (2013.01); *C02F 2209/005* (2013.01); *C02F 2209/40* (2013.01); *Y02E 50/343* (2013.01)

(58) Field of Classification Search
CPC .. C02F 11/04; C02F 3/28; C02F 1/385; C02F 2209/40; C02F 2209/005; C12P 5/023; B09B 3/00
USPC .......... 210/603, 614, 631, 252, 259
See application file for complete search history.

(56) References Cited

U.S. PATENT DOCUMENTS

| | | | |
|---|---|---|---|
| 2,657,831 A | 11/1953 | Pierce | |
| 3,089,601 A | 5/1963 | Chaney et al. | |
| 3,702,128 A | 11/1972 | Trotter, Jr. | |
| 4,053,394 A | 10/1977 | Fisk | |
| 4,089,300 A | 5/1978 | Keen et al. | |
| 5,116,574 A * | 5/1992 | Pearson | A61L 11/00 210/173 |
| 5,377,917 A | 1/1995 | Wiljan et al. | |
| 5,568,996 A | 10/1996 | Buehler | |

(Continued)

OTHER PUBLICATIONS

First Amended Complaint, Redacted Version, *Marco Doda, et al.* v. *Waste Management, Inc., et al*, (D. Del.), 17-Cv-00604-GMS), 52 pages, Aug. 7, 2017.

"Waste Management of Orange County, Orange FoodPower$^{sm}$" presented at the Orange County, California Sanitation District on Apr. 12, 2010.

Webpage from Ecco-Technologies' website Oct. 4, 2009 illustrating the "eCorrect" machine.

(Continued)

*Primary Examiner* — Fred Prince
(74) *Attorney, Agent, or Firm* — Greenberg Traurig LLP

(57) ABSTRACT

An organic waste processing system and method for producing an organic waste slurry for the production of bio-gas, transportation fuels or chemical products, wherein the system and method produces an organic waste slurry having substantially ten to fifteen percent in total solids and high levels of COD.

27 Claims, 8 Drawing Sheets

(56) References Cited

U.S. PATENT DOCUMENTS

| | | | |
|---|---|---|---|
| 5,791,566 A | * | 8/1998 | Higo ................ C10L 1/326 |
| | | | 241/20 |
| 6,267,309 B1 | | 7/2001 | Chieffalo et al. |
| 6,536,602 B2 | | 3/2003 | Ruescher et al. |
| 7,163,629 B2 | | 1/2007 | Abu-Orf et al. |
| 7,410,583 B2 | | 8/2008 | Gray (Gabb) et al. |
| 7,811,456 B2 | | 10/2010 | Choate et al. |
| 2003/0171636 A1 | | 9/2003 | Hood et al. |
| 2008/0023397 A1 | | 1/2008 | Clifford et al. |
| 2008/0203014 A1 | | 8/2008 | Magner et al. |
| 2010/0078519 A1 | | 4/2010 | Pall et al. |
| 2010/0264079 A1 | | 10/2010 | Begin et al. |

OTHER PUBLICATIONS

Webpage from www.ecco-technologies.com/somat.html and pdf from that webpage for Somat Model: ET-100w.
Letter and Attachments, dated Oct. 14, 2016, from Ada Doda, CEO of Doda USA, Inc.
Letter, dated Oct. 28, 2016, from Ben D. Tobor to Ada Doda.
Letter and Attachments, dated Nov. 7, 2016, from Patrick J. Rooney to Ben D. Tobor.
Letter and Attachments, dated Jan. 13, 2017, from Ben D. Tobor to Patrick J. Rooney.
Presentation made by Doda U.S.A. Inc. entitled "Equipment Configurations for Contaminant Removal and Reduction" at the BioCycle West Coast Conference in San Diego, California, in Apr. of 2010.

\* cited by examiner

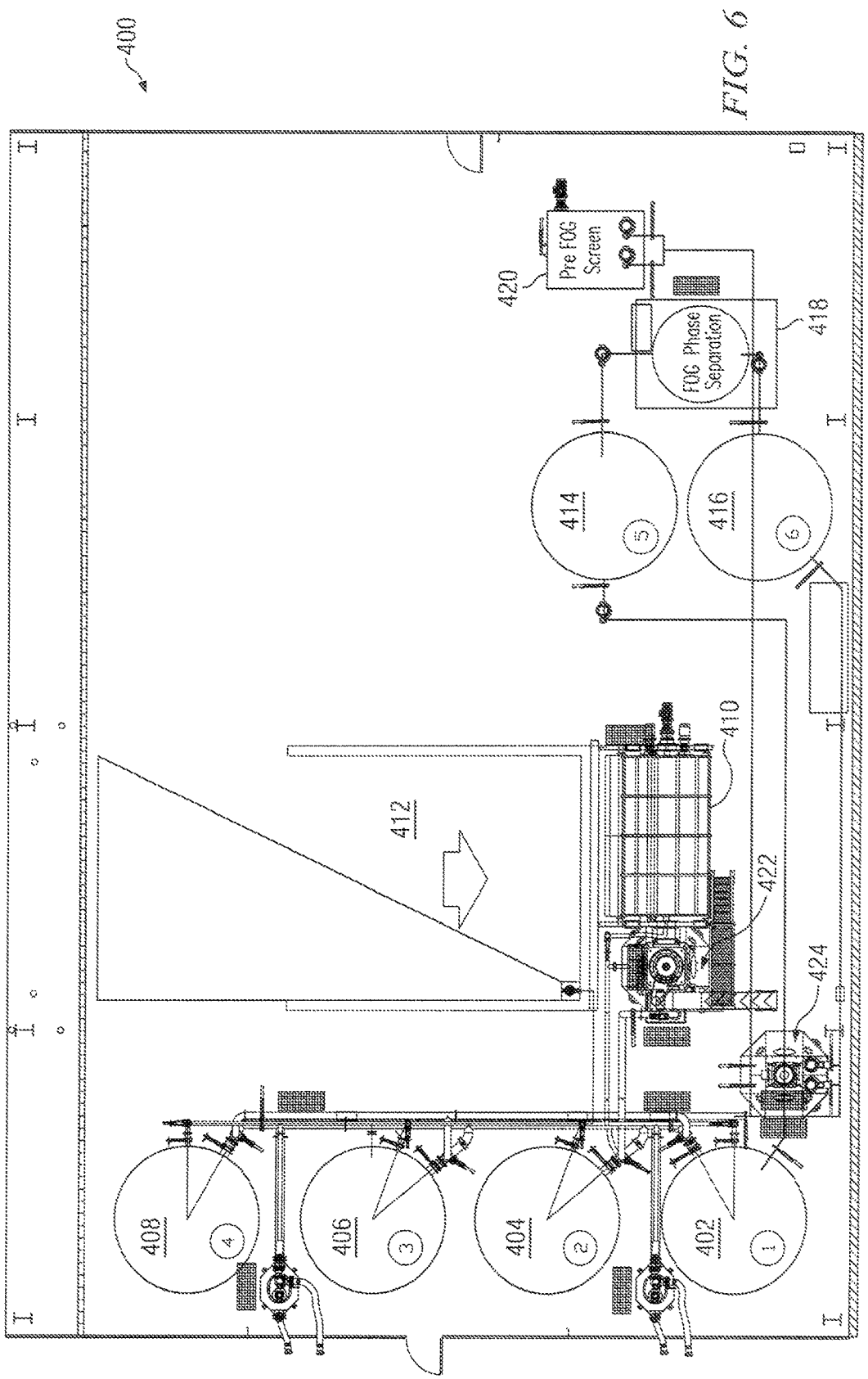

SYSTEM AND METHOD FOR CONVERTING ORGANIC WASTE INTO METHANE AND OTHER USEFUL PRODUCTS

RELATED APPLICATION

This application claims the benefit, and priority benefit, of U.S. patent application Ser. No. 14/589,215, filed Jan. 5, 2015, which was a continuation of U.S. patent application Ser. No. 13/169,843, filed Jun. 27, 2011, entitled "System and Method for Converting Organic Waste Into Methane and Other Useful Products", now U.S. Pat. No. 8,926,841, issued Jan. 6, 2015. This present application is a continuation of U.S. patent application Ser. No. 14/589,215, filed Jan. 5, 2015.

FIELD OF THE INVENTION

The present invention is generally related to the processing of municipal solid waste, and more particularly to a system and method for converting organic waste into methane for energy production or the production of other useful transportation fuel and chemical products.

DISCUSSION OF THE BACKGROUND

Waste disposal is an issue faced by nations across the world. In recent history, waste has primarily been disposed of in landfills, which require substantial land, engineering and environmental monitoring and management resources. Regulatory and political bodies, as well as generators of waste, are increasingly interested in reducing waste volumes, diverting wastes from landfills and incinerators while promoting the more sustainable use of waste products. It is therefore desirable to develop technologies that not only reduce the amount of landfilled and incinerated waste, but also to capture and use such material for beneficial purposes.

Recently, recycling and composting of residential and commercial waste materials has become a preferred way to reduce the amount of waste materials that would otherwise be directed to landfills. Although there is some variation among geographic regions, it has become common to recycle paper, metals, glass and plastic materials. More recently, organic materials such as green waste (e.g., tree and grass clippings) and food waste are being commercially composted for use as a soil amendment or occasionally utilized for the generation of methane gas. However, current compost practices produce products of limited commercial value, and the known techniques utilizing organic materials from a municipal waste stream in an anaerobic digestion process have failed to achieve consistent, high levels of methane production.

Thus, there currently exist deficiencies associated with waste processing, and, in particular, with organic waste processing.

SUMMARY OF THE INVENTION

Accordingly, one aspect of the present invention is to provide an organic waste processing system to produce a slurry for the production of bio-gas, transportation fuels and chemical products, and a residual solid. The system includes (i) a hopper configured to receive sorted organic waste having contaminants from one or more sources, (ii) a separator system in communication with the hopper and configured to receive the sorted organic waste from the hopper and to remove at least a portion of the contaminants in the sorted organic waste, (iii) a complimentary liquid tank in communication with the separator system and containing complimentary liquids, (iv) a wash water liquid tank in communication with the separator system and containing wash water, (v) a product tank in communication with the separator system and configured to receive the sorted organic waste from the separator system, (vi) a make-up product tank in communication with the separator system and configured to receive the sorted organic waste from the separator system having low COD, (vii) a anaerobic digestor system configured to receive the sorted organic waste from the product tank, and (viii) a programmable logic controller. The separator system includes a primary centrifugal separator. At least a portion of the complimentary liquids from the complimentary liquid tank is periodically injected into the separator system upon request. At least a portion of the wash water from the wash water tank is periodically injected into the separator system upon request. At least a portion of the organic waste from the make-up product tank is periodically injected into the product tank upon request. The anaerobic digestor system includes a flow meter, a control valve and an anaerobic digestor tank. The control valve has an open and close position. The programmable logic controller is configured to periodically inject organic waste into the anaerobic digestor tank to enhance anaerobic digestion. The programmable logic controller is configured to monitor the flow meter and to open and close the control valve to inject the organic waste into the anaerobic digestor tank.

Another aspect of the present invention is to provide a method for producing a slurry for the production of bio-gas, transportation fuels and chemical products, and a residual solid. The method includes (i) receiving, into a hopper, sorted organic waste having contaminants from one or more sources, (ii) receiving, into a separator system in communication with the hopper, at least a portion of the sorted organic waste from the hopper and removing at least a portion of the contaminants in the sorted organic waste, (iii) periodically injecting, from a complimentary liquid tank having complimentary liquid, at least a portion of the complimentary liquids into the separator system upon request, (iv) periodically injecting, from a wash water liquid tank having wash water, at least a portion of the wash water into the separator system upon request, (v) receiving, into a product tank in communication with the separator system, at least a portion of the sorted organic waste from the separator system, (vi) receiving, into a make-up product tank in communication with the separator system, at least a portion of the sorted organic waste from the separator system, (vii) periodically injecting, into the product tank, at least a portion of the organic waste from the make-up product tank upon request, (viii) receiving, into a anaerobic digestor system, the sorted organic waste from the product tank, (ix) anaerobic digesting the organic waste in the anaerobic digestor tank, (x) controlling the flow of the organic waste into the anaerobic digestor tank to enhance anaerobic digestion. The separator system includes a primary centrifugal separator. The make-up product tank receives organic waste having a low COD. The anaerobic digestor system includes a flow meter, a control valve and an anaerobic digestor tank, wherein the control valve has an open and close position. The flow is controlled by a programmable logic controller that is configured to periodically inject organic waste into the anaerobic digestor tank. The programmable logic controller is configured to monitor the flow meter and to open and close the control valve to inject the organic waste into the anaerobic digestor tank.

BRIEF DESCRIPTION OF THE DRAWINGS

A more complete appreciation of the present invention and many of the attendant advantages thereof will be readily obtained as the same becomes better understood by reference to the following detailed description when considered in conjunction with the accompanying drawings, wherein:

FIG. 6 is a plan view of an exemplary organic waste processing apparatus in accordance with an embodiment of the present invention.

DETAILED DESCRIPTION OF THE PREFERRED EMBODIMENTS

Figure 1:
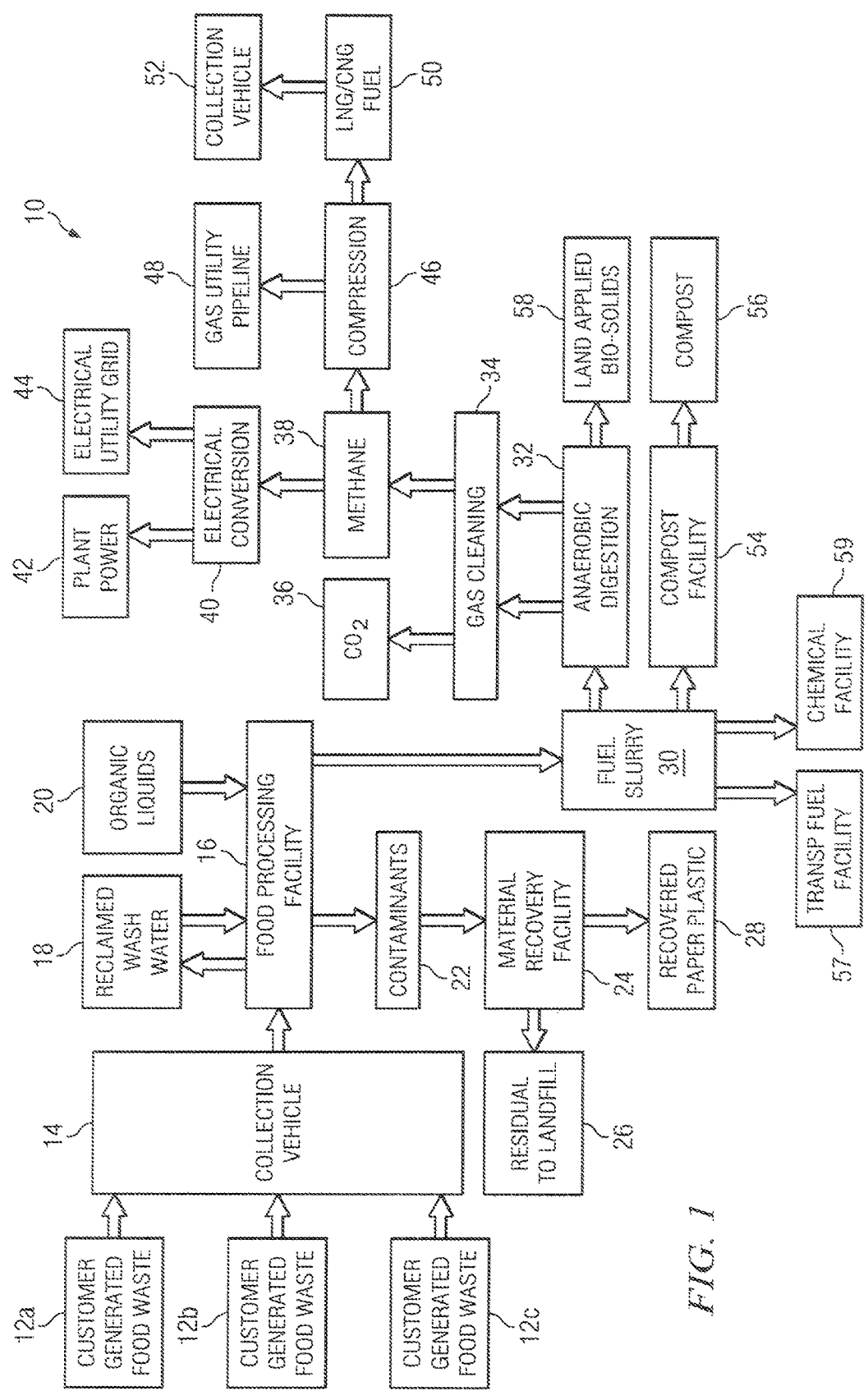
FIGS. 1-4 are block diagrams illustrating organic waste processing in accordance with an embodiment of the present invention.

Referring now to the drawings, wherein like reference numerals designate identical or corresponding parts throughout the several views, preferred embodiments of the present invention are described.

The present invention provides a system and method for converting organic waste materials into a uniform fuel product, also referred to herein as feedstock, that is suitable for anaerobic digestion to produce bio-gas, transportation fuels and/or chemical products and a residual solid.

There are four general stages in the anaerobic methanogenesis process: hydrolysis, acidogenesis, acetogenesis, and methanogenisis. Organic waste is typically delivered to the waste processing facility in the initial stages of hydrolysis. Once processing begins, organic waste moves from the hydrolysis stage to the acidogenesis stage. The pH level goes from approximately 5.0 to approximately 4.0 during the first day. Continued aeration and recirculation brings the material to a pH of less than approximately 3.7. The organic waste is in the acidogenesis stage once the pH level is approximately 3.6. This typically takes approximately three to four days after the initial processing step. During this initial three day period, the COD moves from approximately <200 g/L to <160 g/L. Essentially, the available organics are being digested.

After approximately 2 to 3 days, the organic waste takes on a vinegar like smell. At this point the organic waste is liquid enough to be used as wash water again. Using the organic waste as wash water increases the fuel product's pH and the COD. However, after approximately 24 to 48 hours the product returns to the acidogenesis phase and the pH and COD decrease significantly. Generally, the longer the product stays in the tank or in the digester feed station the less gas the product will produce.

According to at least one embodiment, a processing facility receives organic waste that is source separated, meaning it has been separated from general solid waste. Such organic materials may be collected from commercial and/or consumer sources, such as grocery stores, hotels, restaurants, schools, food processing facilities, residential homes, and the like.

Organic waste materials may contain contaminates which must be screened and otherwise separated. Such non-digestible contaminates include, without limitation, plastic, glass, ceramics, bones, seeds, cardboard, and the like. Through the use of one or more centrifugal separators as well as sorting and screening, source separated organic materials are slurried and cleaned of these non-digestible contaminates. According to at least one embodiment, a "primary separator" and a "secondary separator" are utilized. The resulting slurried organic waste is a uniform fuel product that is suitable for use in the anaerobic digestion process to produce bio-gas and a residual solid.

Liquids with organic strength may be added during the contaminate removal process for use as a screen wash water. Liquids with organic strength may also be added during the anaerobic digestion process to compliment the fuels benefits in the anaerobic digester. Liquids with organic strength can be obtained by separating such material from its container, such as milk from a container, or receiving them in bulk tankers. According to at least one embodiment, the organic liquids are stored in holding tanks prior to use in a centrifugal separator or anaerobic digester.

Ideally, although not required, the cost associated with the processing, transport and ultimate disposal of the organic waste materials pursuant to the present invention should be equal to or less than the cost for traditional waste disposal, such that the cost is at least neutral to the customer. The source separation and collection program should also be easy for the customer to implement. The energy benefits of the organic waste material, such as, without limitation, renewable, electricity revenues, transportation fuel revenues, beneficial chemical products revenue, and gas commodity revenues, are captured.

Using the present invention, it is possible to (i) produce consistent, high quality feedstock that can be safely added to an anaerobic digestion process, or fuel/chemical process and which will increase methane gas production, transportation fuels, other beneficial chemicals, and (b) maximize diversion of organic waste from landfills.

An important consideration in the anaerobic digestion process is the controlled addition of feedstock to minimize stress on the biologic process. In the case of municipal bio-solids digesters, significant stress on the biology in the digester may cause a complete breakdown of the process, requiring the unit being taken off line and cleaned out. Therefore, waste processing facilities are often cautious about introducing material other than bio-solids to their digesters.

Although food waste has been shown to benefit methane gas production in an anaerobic digestion process, its use has been limited due to contamination (e.g., tableware and packaging) and inconsistent organic properties. It is therefore important to separate contaminants from the organic waste, and create a fuel with consistent chemical properties.

I. Organic Waste Categorization System

Methane gas production from an anaerobic digester is improved by the addition of materials with high amounts of chemical oxygen demand (COD). The addition of food waste, which typically has a COD higher than bio-solids, to the anaerobic digestion process increases methane gas production. However, not all food waste has the same COD. For instance, fats, oils, and greases (FOG) typically have a very high COD. Food waste with low FOG content typically has a low COD.

High-FOG food waste generally originates from post-consumer entities, such as restaurants. Low-FOG food waste generally originates from pre-consumer entities, such as grocery stores and food processing facilities. However, grocery stores with deli's may also have high-FOG food waste.

According to at least one embodiment, the organic waste is classified into one of three categories based on its collection point: (i) pre-consumer materials (PrC), (ii) post-consumer high FOG (PCHF), and (iii) post-consumer low FOG (PCLF). Obviously, additional categories are possible to provide greater precision in food waste recipes within the scope of the present invention. For example, other possible "complimentary liquids" include grease trap material, deceased consumer products, off-spec consumer products, and beverage industry industrial process waste waters.

II. Multi-Tank Food Waste Blending System

Figure 2:
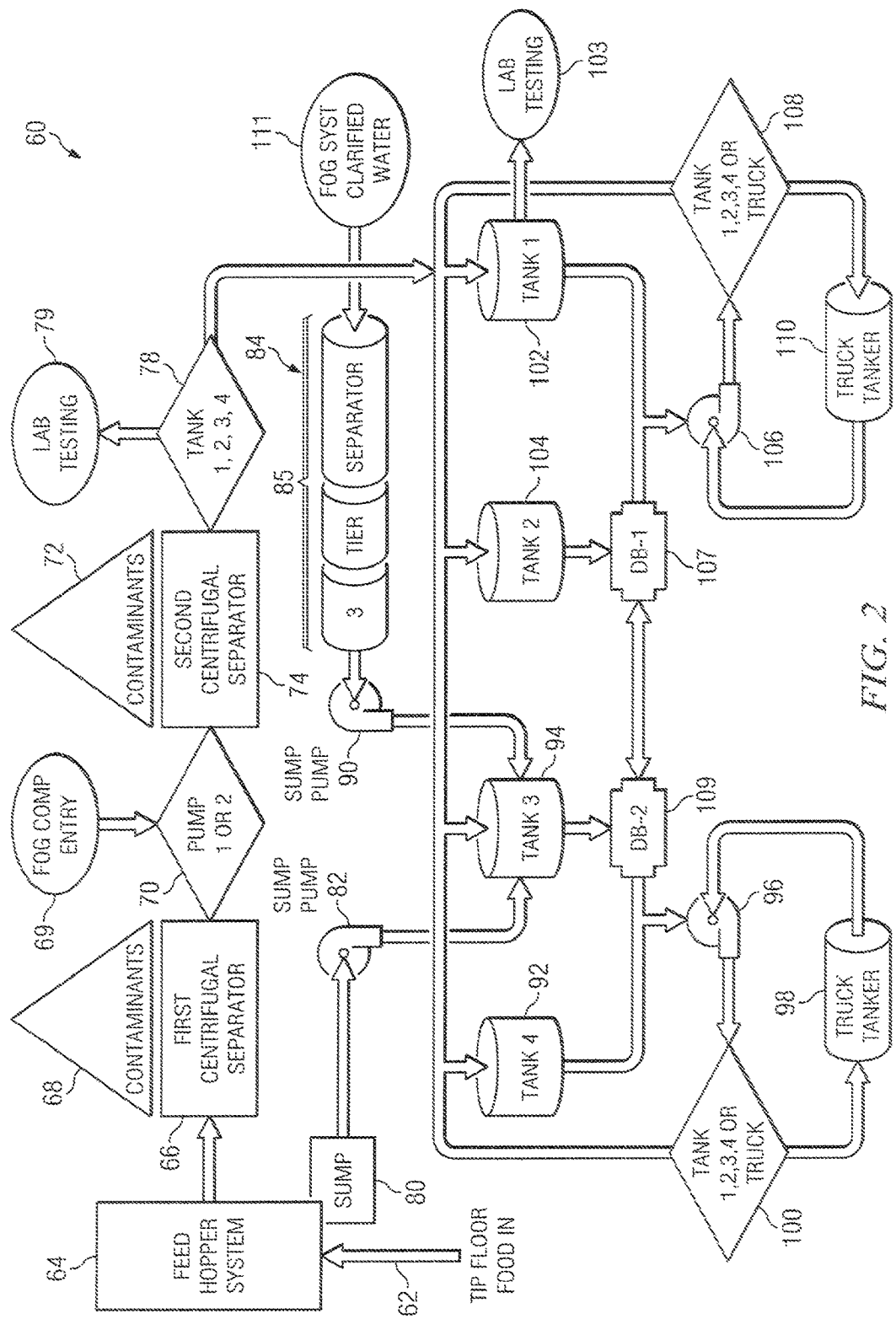
Figure 3:
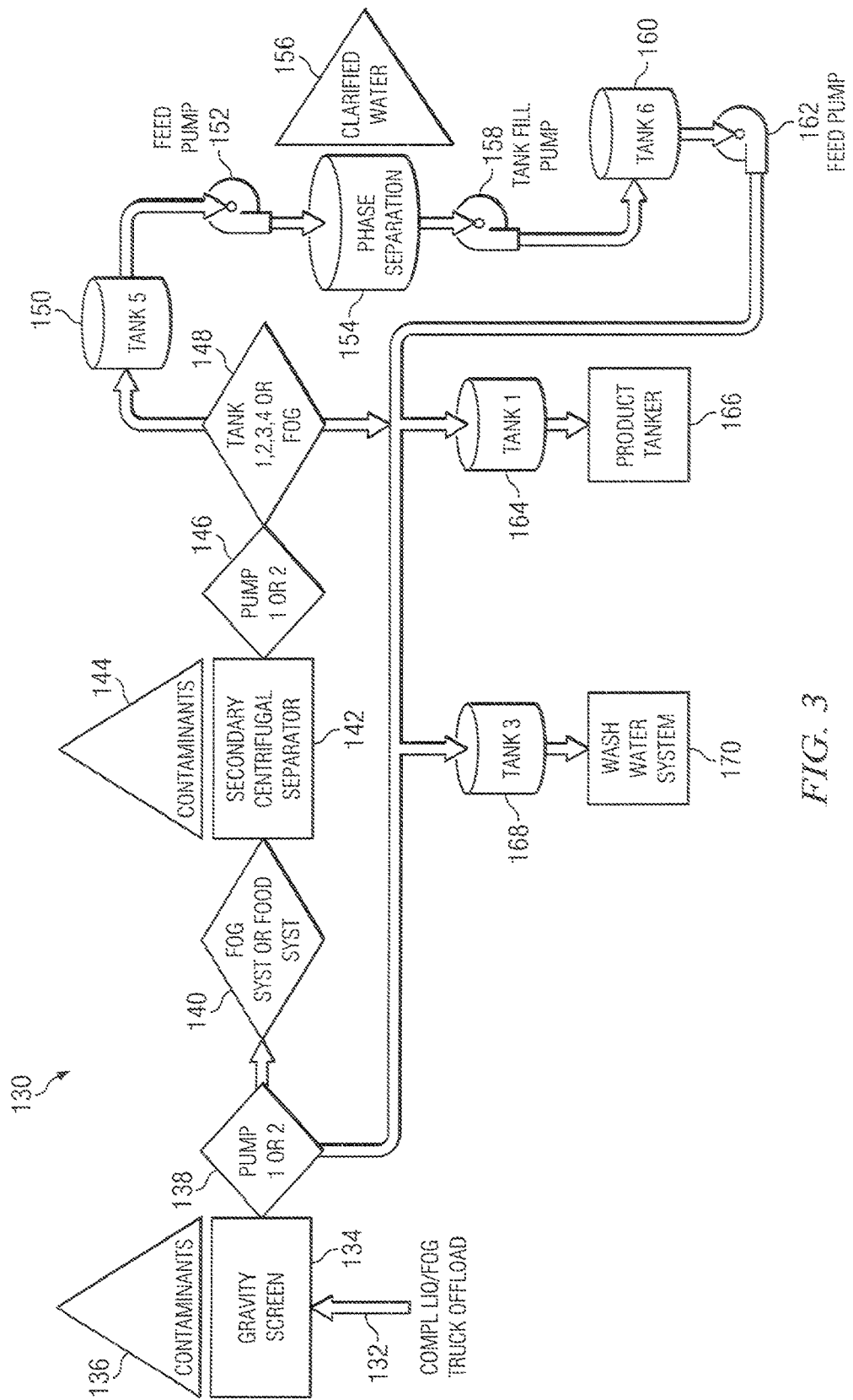

The present invention utilizes a multi-tank system which allows for the acceptance, processing and beneficial use of a very high percentage of organic waste. The multi-tank system of the present invention produces a consistent fuel product and reduces the amount of landfilled waste. According to at least one embodiment 400 of FIG. 6, four or more twelve-thousand gallon storage tanks are utilized, including, without limitation, (i) a final product tank (Tank 1) (402), or 102 (FIG. 2), (ii) a make-up product tank (Tank 2) (404), or 104 (FIG. 2), (iii) a wash water tank (Tank 3) (406), or 94 (FIG. 2), and (iv) a complimentary liquids tank (Tank 4) (408), or 92 (FIG. 2). Optionally, in addition to the four above-identified tanks, two additional twelve-thousand gallon storage tanks are utilized, including, without limitation, (v) a raw FOG liquids tank (Tank 5) (414), or 150 (FIG. 3), and (vi) a phase separated FOG liquids tank (Tank 6) (416), or 160 (FIG. 3). All of the storage tanks are designed for recirculation. A compressed air line on the fill side of each tank induces air during the recirculation process. The tanks are set on a reinforced concrete slab for use as a foundation. Liquids are periodically added to the organic waste to clean screens in the centrifugal separators and make the product capable of being pumped.

Tank 1

Still with reference to FIG. 6, Tank 1 (402) contains food waste slurry suitable for use as anaerobic digestion feedstock. Based on current findings by the inventors of the present invention, according to at least one embodiment, Tank 1 (402) should contain organic waste slurry having substantially (i) ten to fifteen percent in total solids, and (ii) high levels of chemical oxygen demand (COD). The content of Tank 1 is blended from (i) material processed from the primary separator 422, or 66 (FIG. 2) and/or secondary separator 424, or 74 (FIG. 2) or 142 (FIG. 3), (ii) Tank 2 (404), (iii) Tank 5 (414) and/or (iv) Tank 6 (416). According to one embodiment, Tank 1 (402) is never emptied out. Instead, organic waste is continually blended in from the above-identified sources. According to at least one embodiment, before the organic waste is removed from Tank 1 (402) for anaerobic digestion use, it is tested, without limitation, for (i) total solids, (ii) volatile solids, (iii) raw fats, oils, and greases (FOG), (iv) pH, (v) dissolved oxygen, (vi) conductivity, (vii) chemical oxygen demand, (viii) total organic carbon, and (ix) total Kjeldahl nitrogen.

Tank 2

Tank 2 (404) contains slurry not yet suitable for use as anaerobic digestion feedstock. The content of Tank 2 (404) is from the primary separator 422 and/or secondary separator 424. The content of Tank 2 (404) is blended into Tank 1 (402) as needed.

Tank 3

Tank 3 (406) contains liquid not yet suitable for anaerobic digestion use, but which can be injected into the primary separator 422 and/or secondary separator 424 as wash water to thin the organic waste slurry and clean the screen, or Tank 1 (402) as an organic waste slurry thinner. The content of Tank 3 (406) is from the primary separator 422, secondary separator 424 and/or sumps.

Tank 4

Tank 4 (408) contains liquid not yet suitable for anaerobic digestion use, but which can be injected into the primary separator 422 and/or secondary separator 424 as wash water and/or blended with materials to create a suitable anaerobic digestion feedstock. The content of Tank 4 (408) is from the primary separator 422, secondary separator 424 and/or inbound tanker trucks 132 (FIG. 3).

Tank 5

Tank 5 (414), 150 (FIG. 3), contains cleaned FOG that has been generally cleaned of solids in the secondary separator 424, 142 (FIG. 3). Once stored in tank 5 (414), the FOG is then sent to a FOG Phase-Separation System 418, 154 (FIG. 3). The content of Tank 5 (414) is also used for wash water in both the primary and secondary separators 422, 424. The FOG 132 (FIG. 3) may be first off loaded by a FOG truck offload system, with a pre-screen 420, 134 (FIG. 3).

Tank 6

Tank 6 (416) accepts FOG processed by the FOG Phase-Separation System, or FOG Separation System 418. The FOG Separation System 418 processes FOG liquids that have been processed through the secondary separator 424. The purpose of FOG Separation System 418 is to separate FOG from water. The water, or clarified water, once separated, is discharged to a sanitary sewer or sent to Tank 3 (406) for use as wash water, and the FOG is directed to Tank 6 (416). The content of Tank 6 (416) is injected into Tank 1 (402) as necessary to increase the chemical oxygen demand (COD) of the feedstock product.

By means of the present invention, virtually any type of organic waste, including undesirable (low COD) material, may be processed. Rather than landfilling or composting (which is less efficient than anaerobic digestion and other chemical processes with respect to energy creation), undesirable material may be stored and gradually blended-in with organic waste having a higher COD using the multi-tank arrangement of the present invention to create a uniform fuel product. Not only does less material get landfilled, but the environmental impacts and costs involved with transporting waste material to another facility for subsequent disposal or composting are avoided.

Further, a consistently high quality organic waste fuel product, or "feedstock," is produced that digester facilities are seeking. Having multiple tanks allows a waste processing facility to control recipes of fuel product such that there are no significant fluctuations in content based on the organic waste that is delivered to, and processed by, the waste processing facility. The present invention allows for consistent production of both solids and COD levels in the final blended fuel product.

III. Organic Waste Processing Considerations

There are several factors that should be considered in the processing of organic waste. The organic waste may be very odiferous and should be processed quickly to manage the odors. In fact, such odor management is often required by waste processing facility permits. Ideally, although not limiting, all equipment contacted by the organic waste is sanitized or cleaned with hot water at least once per shift to mitigate odors. Tip floors 412 (FIG. 6) or 62 (FIG. 2) and equipment, such as a hopper or feed hopper system 410 (FIG. 6) or 64 (FIG. 2), require more frequent sanitization depending on the degree of odor. This sanitizing may be accomplished by several means: (i) a hose system that is configured and sized to accommodate enough quantity of heated water of an appropriate volume and temperature to wash down the tipping floor 412 and equipment 410; and/or (ii) a power washer, such as a Hotsy hot water power washer, may also be used for sanitizing the system.

In order to maintain cleanliness and to reduce odors, according to at least one embodiment, the tipping area is configured to be small such that the facility is required to process the organic waste material quickly to keep it from being stored on the tipping floor area.

The feeder unit is configured for easy loading and to tip over for easy cleanout if the feeder screws jam. According to at least one embodiment, the tipping area has four-foot walls with a one foot sloped floor for drainage. Contaminants from the centrifugal separator systems are expelled at the top and onto a conveyor that deposits the waste in a roll away to a trash container. The waste volume depends on the contamination levels of the incoming material, but if contamination levels are reduced to less than five percent by weight, then the waste volume is minimal. When the waste container becomes full, it is exchanged with an empty container. Contents of the full waste container are rolled away for disposal or recycling.

When a tank is filled with processed organic fuel or other materials, the air within the tank is displaced. According to at least one embodiment, all displaced air is run through a bio-filter made with a thirty-yard roll off box filled with wood chips to mitigate odors when filling tanks. Bio-airc bio-filter supports were installed in the bottom of the thirty-yard roll off box as a plenum.

According to at least one embodiment, a four zone NCM Odor & Dust Control misting system is installed so that the odorant can be applied incrementally to reduce odor. Zone 1 covers the tip floor. Zone 2 covers the rest of the inside of the building. Zone 3 covers the building open front area. Zone 4 covers the truck load out area.

According to at least one embodiment, the organic waste processing system is configured with redundancy. The system can transfer product with one of multiple transfer pumps. The system is configured to load tanker trucks, and unload tanker trucks. This may is accomplished by pumping or by other means from any tank to the tanker truck.

According to at least one embodiment, all water used to clean the organic waste processing facility is captured and either reused as wash water or blended into the fuel product to create a thinner consistency. Complimentary liquids received are stored in Tank 4 for later use as wash water or blended into fuel product to achieve the desired recipe.

According to at least one embodiment, unprocessed FOG is accepted and used as both wash water and for COD enhancement in the final product. The FOG material can be subjected to a heat source in Tanks 5 and 6 such that the FOG does not congeal.

IV. Control Systems

All fuel processing system functions are controlled by a programmable logic controller (PLC). The PLC has several control screens that allow for operation of the processing system in several different modes. The systems and equipment can be operated manually or automatically as a result of a selected process. Automatic operation of the system is accomplished by accessing a user interface customized for the particular type of process, including, without limitation, food processing, FOG processing, decasing, truck load and unload, and tank recirculation. Manual control of each individual piece of equipment is accessed by manual screens behind the equipment subgroup page. Alarms are set for various conditions requiring user attention.

The PLC includes ladder-style logic program embodied on the touch screen PLC controller. The PLC controls a combination of both remote and local input and output (IO) modules which in turn control the hardware components in the system, including, without limitation, starters, variable frequency drives, soft start starters, hydraulic control valves and the like. The PLC ladder-style control logic program defines the control strategy and the functionality of the system.

A supervisory control and data acquisition (SCADA) interface is configured to control of the system remotely over the internet. The SCADA system allows the use of all the user input and data reporting functions of the PLC. The SCADA system can be integrated into the sites existing SCADA System allowing control of the system remotely in the sites control room.

According to at least one embodiment, the fuel processing system PLC is configured to sense and coordinate valve movements and to start and stop motors depending on the particular operation the operator has chosen to do. The main process configurations include, without limitation: process food; process FOG; recirculate tanks; load transfer tanker; and unload transfer trailer. Each of the previous screens allow the user to choose which pumps to use; choose which tank to fill; choose which tank to use for wash water. During tank transfer operations the screen allows for; transfer liquids; choose distribution box; choose "from" tank; choose "to" tank.

According to at least one embodiment, both the fuel processing system and the digester feed system PLC is setup with manual operators for each valve to run valve diagnostics. The valves are stainless steel knife gate valves that are hydraulically operated, each with two proximity sensors for position sensing. The control topology includes, without limitation, sensors homerun to the control box and landed on IO strips. Alternatively, distributed 10 may be utilized to reduce the number of cables that need to be homerun to the control box.

The digester feed system controls the feed of the prepared fuel, pumped from Tank 1 at the processing facility to a tanker truck and then transported to a digester facility, then pumped from the tanker truck into each digester feed system. To allow for slight inconsistencies in the fuel product that is fed into the digester, alternatively the control system can be updated with the total solids information of the fuel product delivered to the feed system tank. The system calculates the final feed rate based on the TS of the fuel and the TS of the digester primary and TWAS infeed. This balances the TS load of the digester which manages the load transients therefore creating a more stable operating environment.

The digester feed system functions are controlled by a programmable logic controller (PLC). According to at least one embodiment, the PLC has several control screens that allow for operation of multiple digester feed systems. For each feed system, an operator can input the desired digester feed rate in gallons per hour. Once the recirculation pump is started via the PLC, and the feed system start is selected, the feed valve opens and the fuel passes through a flow meter. The flow is measured in gallons by the flow meter. Once the desired feed amount setpoint is reached, the PLC closes the feed valve and waits the remainder of the one hour period for the feed cycle to be restarted. Manual control of each individual piece of equipment is accessed by manual screens behind the equipment subgroup page. Alarms are set for no fuel feed, pump not started, and various other conditions requiring user attention.

According to at least one embodiment, optionally the digester feed system controls the feed of the prepared fuel into each digester using a measured total solids approach. To allow for consistent feed of the fuel product into the digester, the control system is updated hourly with the total solids information of the fuel product in the feed system tank from the total solids sensing device in the tank. The system calculates the final fuel feed rate based on the established total solids feed setpoint which is based on a setpoint percentage of the feed and the total solids feed rate of the digester primary and TWAS infeed. Fuel feed gallons per hour setpoint may be determined using the following equation:

$$RFR=(DSW*S)*FR$$

$$RFFG=RFR/FSW$$

In the above equation, DSW represents the primary & TWAS dry solids weight, S represents the desired fuel solids percentage, FR represents primary & TWAS feed rate per hour, RFR represents the required fuel solids feed rate per hour, FSW represents the weight of fuel solids per gallon, and RFFG represents the required fuel feed gallons per hour.

By programmatically controlling the feed valve, the total solids load of the digester is better balanced and the load transients are managed thereby creating a more stable operating environment.

The PLC controlled digester feed system communicates with the waste processing facility's supervisory control and data acquisition system (SCADA). All functions, setpoints, and alarms programmed into the PLC are available to the facilities control room via a SCADA communications interface.

V. Organic Waste Processing

Block diagrams 10, 60, 130, and 180 illustrating organic waste processing in accordance with an embodiment of the present invention are shown in FIGS. 1-4. As shown in FIG. 1, commercial and/or consumer generated organic waste is collected from one or more sources 12a-12c via one or more collection vehicles 14, such as waste trucks or other similar carriers, and deposited at food processing facility 16. The organic waste may be collected from commercial and/or consumer sources such as grocery stores, hotels, restaurants, schools, food processing facilities, residential homes, and the like. According to at least one embodiment, the food waste is classified into, without limitation, one of three categories based on its collection point: (i) pre-consumer materials (PrC), (ii) post-consumer high FOG (PCHF), and (iii) post-consumer low FOG (PCLF). High-FOG food waste typically originates from post-consumer entities, such as restaurants. Low-FOG food waste typically originates from pre-consumer entities, such as grocery stores and food processing facilities.

The food waste processing facility 16 processes the organic waste into fuel slurry 30, as more detailed in FIG. 2. Reclaimed wash water 18 and organic liquids 20 are utilized during this processing. Contaminants 22 contained with the organic waste are removed and may be further processed and recovered at a material recovery facility 24. For instance, paper and/or plastic 28 may be recovered from the contaminants 22. Non-recoverable contaminants 22 are sent to a disposal facility 26.

The fuel slurry 30 may be sent to a compost facility 54 to be used in the generation of compost 56. Otherwise, the fuel slurry 30 may be further processed by means of anaerobic digestion 32 to produce carbon dioxide ($CO_2$) 36 and methane 38, or land applied bio-solids 58. Such processing may include gas cleaning 34 and/or separating any gasses generated by means of the anaerobic digestion 32. The carbon dioxide ($CO_2$) 36 and methane 38 may be converted to electrical energy 40 to power a plant 42 or electrical utility grid 44.

The methane 38 may also be cleaned 34 and compressed 46 and transmitted via a gas utility pipeline 48. The methane 38 may also be used as LNG/CNG fuel 50 and transported via collection vehicle 52. The fuel slurry may also be sent to a transportation fuel facility 54 or a chemical facility 59.

As shown in FIG. 2, at the food waste processing facility 16, the organic waste is unloaded at a tipping area, or tip floor, at the waste processing facility and fed into a hopper, or feed hopper system, as indicated at blocks 62 and 64. One or more centrifugal separators may be used to separate non-digestible contaminates, as indicated at blocks 66, 68, 70, 72 and 74. According to the non-limiting embodiment shown in FIG. 2, a primary, or first, centrifugal separator 66 separates non-digestible contaminates 68 from the semi-processed organic slurry. Such non-digestible contaminates include, without limitation, plastic, glass, ceramics, bones, seeds, cardboard, and the like. Through the use of a centrifugal separator, as well as sorting and screening, source separated organic waste is slurried and cleaned of these non-digestible contaminates. The semi-processed organic slurry is then directed to a second, or secondary, centrifugal separator 74 which further separates non-digestible contaminates 72 from the semi-processed organic slurry. Using two or more centrifugal separators allows for a greater reduction in contaminants. For example, and without intending to limit the present invention, the primary centrifugal separator 66 may be configured to remove contaminants greater than 15 millimeters whereas the secondary centrifugal separator 74 may be configured to remove contaminants greater than 8 millimeters. According to one non-limiting embodiment, the semi-processed organic slurry is directed to a secondary centrifugal separator 74 by means of one or more pumps, which may be selectable at decision block 70. A portion of the semi-processed organic slurry may be tested, as indicated at block 79. FOG wastes, or FOG components, may also enter the secondary centrifugal separator 74 as indicated at block 69.

A determination is made as to which tank the semi-processed organic slurry is directed at decision block 78. The semi-processed organic slurry is then pumped using pumps into an appropriate tank. For example, the semi-processed organic slurry may be pumped to Tank 1 (102), Tank 2 (104), Tank 3 (94) and/or Tank 4 (92). Distribution box 1 (DB-1) (107) may be used to direct the semi-processed organic slurry or the final fuel product to one or more of the above tanks or to a truck tanker 110, by pump 106, and decision block 108. Likewise, distribution box 2 (DB-2) (109) may be used to direct the semi-processed organic slurry or the final fuel product to one or more of the above tanks or to a truck tanker 98, by pump 96, and decision block 100. Any liquids entering sump 80 may be transferred to Tank 3 (94) by sump pump 82. FOG system clarified water, or FOG clarified water 111, may be treated in a separation system 84, such as a 3-tier separation system 85, and sent to Tank 3 (94) by sump pump 90. The final product, or final fuel product, of Tank 1 (102) may be sent for lab testing as indicated at 103.

As shown in FIG. 3, complimentary liquids and/or FOG 132 are directed from a collection vehicle to gravity screen 134 which separates non-digestible contaminates 136. One or more centrifugal separators may be used to further separate non-digestible contaminates 144, as indicated at blocks 142 and 144. According to the non-limiting embodiment shown in FIG. 3, a secondary centrifugal separator 142 separates non-digestible contaminates 144 from the complimentary liquids and/or FOG. Such non-digestible contaminates 144 include, without limitation, plastic, glass, ceramics, bones, seeds, cardboard, and the like. The flow of complimentary liquids and/or FOG 132 from gravity screen 134 may be directed by one or more pumps, which may be selectable at decision block 138, to Tank 3 (168), Tank 1 (164) or for treatment in centrifugal separator 142 as indicated at block 140. A determination is made as to which tank the semi-processed complimentary liquids and/or FOG is directed at decision block 148. The complimentary liquids and/or FOG is then pumped using pumps into an appropriate tank by one or more pumps which may be selectable at decision block 146. For example, the complimentary liquids and/or FOG may be directly pumped to Tank 1 (164), Tank 3 (168) and/or Tank 5 (150) from the secondary separator (142), as determined at decision block 148. The FOG may also be pumped by pump 152 to a FOG Phase-separation unit 154 which separates the FOG from the clarified water 156. The FOG may then be pumped by pump 158 into Tank 6 (160). Liquids in Tank 3 (168) may be used in the wash water system 170. The final product in Tank 1 (164) may be sent to a product tanker 166. FOG in Tank 6 (160) may then be pumped back into the system, if desired, by feed pump 162.

The resulting uniform fuel is suitable for anaerobic digestion to produce bio-gas and a residual solid. A quantity of liquids with organic strength will be added to the contaminate removal process for use as screen wash water to increase the benefits of the fuel. A quantity of liquids with organic strength may also be added to an anaerobic digester to compliment the fuels benefits in the digester. Liquids with organic strength can be obtained by separating the liquids from containers or receiving them in bulk tankers. According to at least one embodiment, the organic liquids are stored in holding tanks prior to use in a centrifugal separator or the anaerobic digester.

Figure 4:
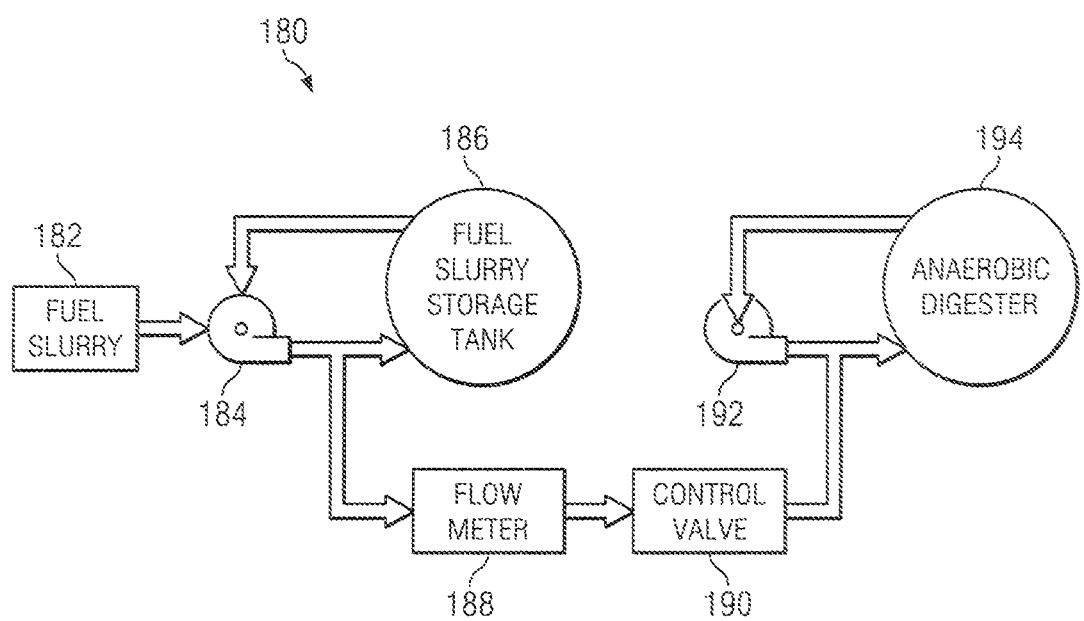

As shown in FIG. 4, the fuel slurry 182 may be directed to a fuel slurry storage tank 186 and/or anaerobic digester 194. According to at least one embodiment, the fuel slurry 182 is initially pumped into to fuel slurry storage tank 186 by means of pump 184. Flow meter 188 opens and closes control valve 190 in a controlled manner such that the fuel slurry 182 is periodically pumped via pump 192 into anaerobic digester 194.

Figure 5A:
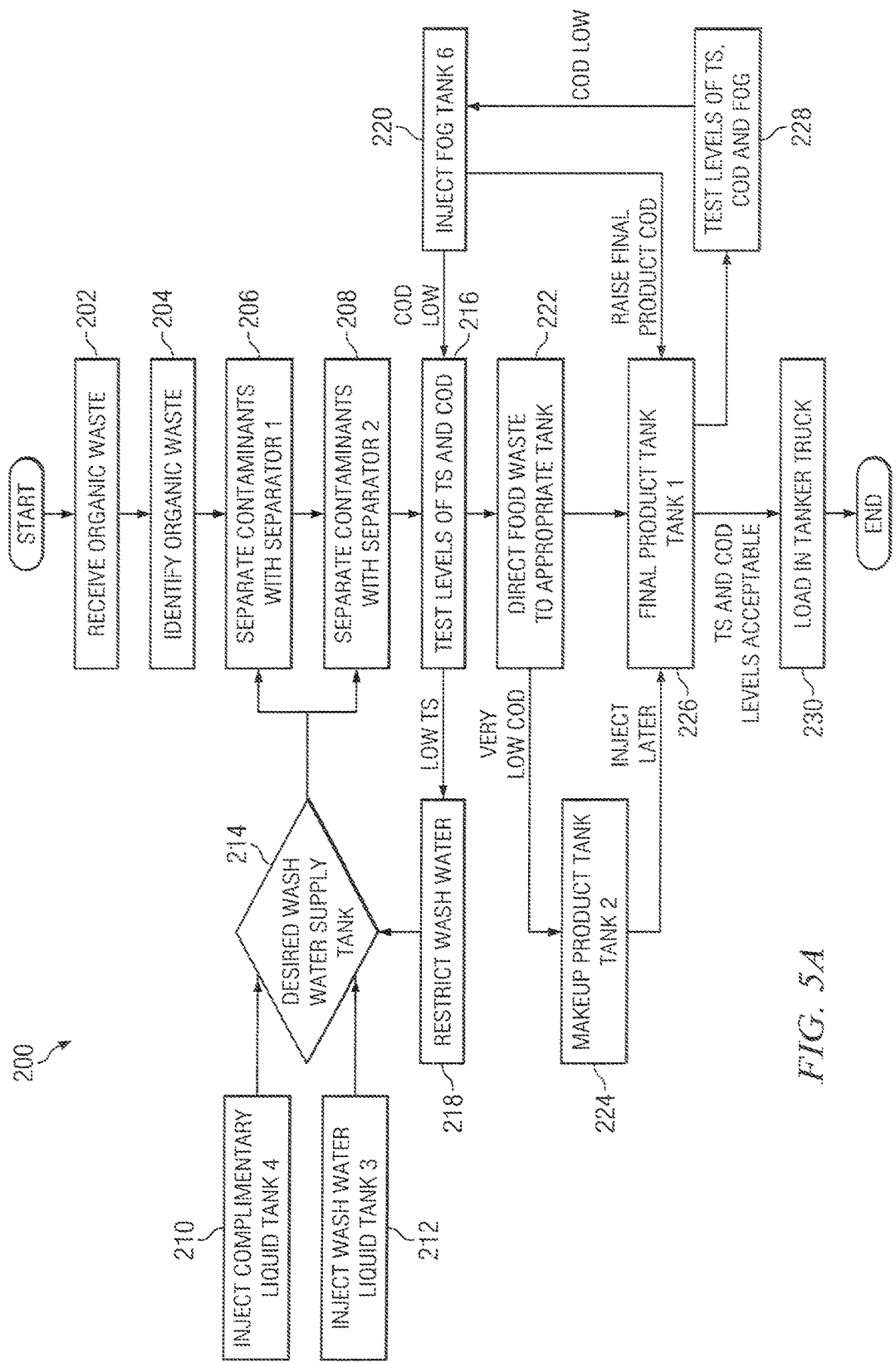
FIG. 5A is a flow chart illustrating organic waste processing in accordance with an embodiment of the present invention.

A flow chart 200 illustrating organic material processing in accordance with an embodiment of the present invention is shown in FIG. 5A. At block 202, unprocessed food waste is received at a processing facility. The organic waste is identified as belonging to one of the three categories described above (PrC, PCHF or PCLF) at block 204.

At blocks 206 and 208, the food waste is then processed by two separation systems to remove contaminants and to reduce the volume of unprocessed food waste into a slurry. According to one non-limiting embodiment, the separation system includes a feeder, a Primary Separator 206 and an optional Secondary Separator 208. Unprocessed food waste is initially dumped into the feeder and then directed to the Primary Separator 206 and then to the Secondary Separator 208. The Primary Separator 206 uses a vertical rotating set of vanes, screen and centrifugal force to extract contaminants (e.g., plastic tableware) and to generate a food waste slurry. The Secondary Separator 208 can also receive liquid wastes (e.g., complimentary liquids, grease trap wastes) directly from a grease trap tanker truck off load system. Similar to the Primary Separator, contaminants are ejected by the Secondary Separator 208, captured in a container and either recycled (if a recyclable material such a paper or plastic) or disposed of. At blocks 210 and 212, complimentary liquid from tank 4 and/or wash water liquid from Tank 3 may be injected into the Primary Separator 206 or the Secondary Separator 208, as indicated by decision block 214.

At block 216, semi-processed organic slurry is tested for the percentages of (i) total solids (TS), (ii) chemical oxygen demand (COD) and (iii) fats, oils, and greases (FOG). The percentage of total solids is determined using a specially calibrated infrared unit. According to at least one embodiment, a semi-processed organic slurry sample is extracted and weighed. The semi-processed organic slurry sample is then dried to remove the water fraction leaving the solids fraction. The difference in weights between the food sample before and after drying is used to determine the percent of total solids.

According to at least one embodiment, the chemical oxygen demand is determined using a standard Hach digestion method and a Hach DR5000 UV-Vis Spectrophotometer system. The result is a correlation between method 8000 results, and a Visible Ultraviolet scan at several wavelengths. The Hach DR5000 UV-Vis Spectrophotometer provides a number that correlates generally to a COD number from the Method 8000 digestion number.

If the total solids are low then wash water is restricted at block 218. If the COD levels are low then FOG from Tank 6 is injected at block 220.

The semi-processed organic slurry is directed to an appropriate storage tank at block 222. According to at least one embodiment, the semi-processed organic slurry is directed to the appropriate storage tank using a pumping mechanism. The semi-processed organic slurry is directed at block 222 to Tank 1 (226) or Tank 2 (224) depending on the COD levels at block 216. Specifically, if the COD is very low then the semi-processed organic slurry is directed to Tank 2. Otherwise, the semi-processed organic slurry is directed to Tank 1. According to at least one embodiment, the semi-processed organic slurry is directed to Tank 1 or Tank 2 using a pumping mechanism. From Tank 1 at block 226, the semi-processed organic slurry may be loaded into a tanker truck, as indicated at block 230.

At block 228, semi-processed organic slurry is again tested for the percentages of (i) total solids (TS), (ii) chemical oxygen demand (COD) and (iii) fats, oils, and greases (FOG) using the method described above. If the COD is low then FOG from Tank 6 is injected at block 220 into Tank 1 (226).

By means of the above, (i) a consistent fuel slurry feedstock is generated that, when added to anaerobic digestion systems, will significantly enhance methane gas production, and (ii) food waste is diverted from landfills.

Figure 5B:
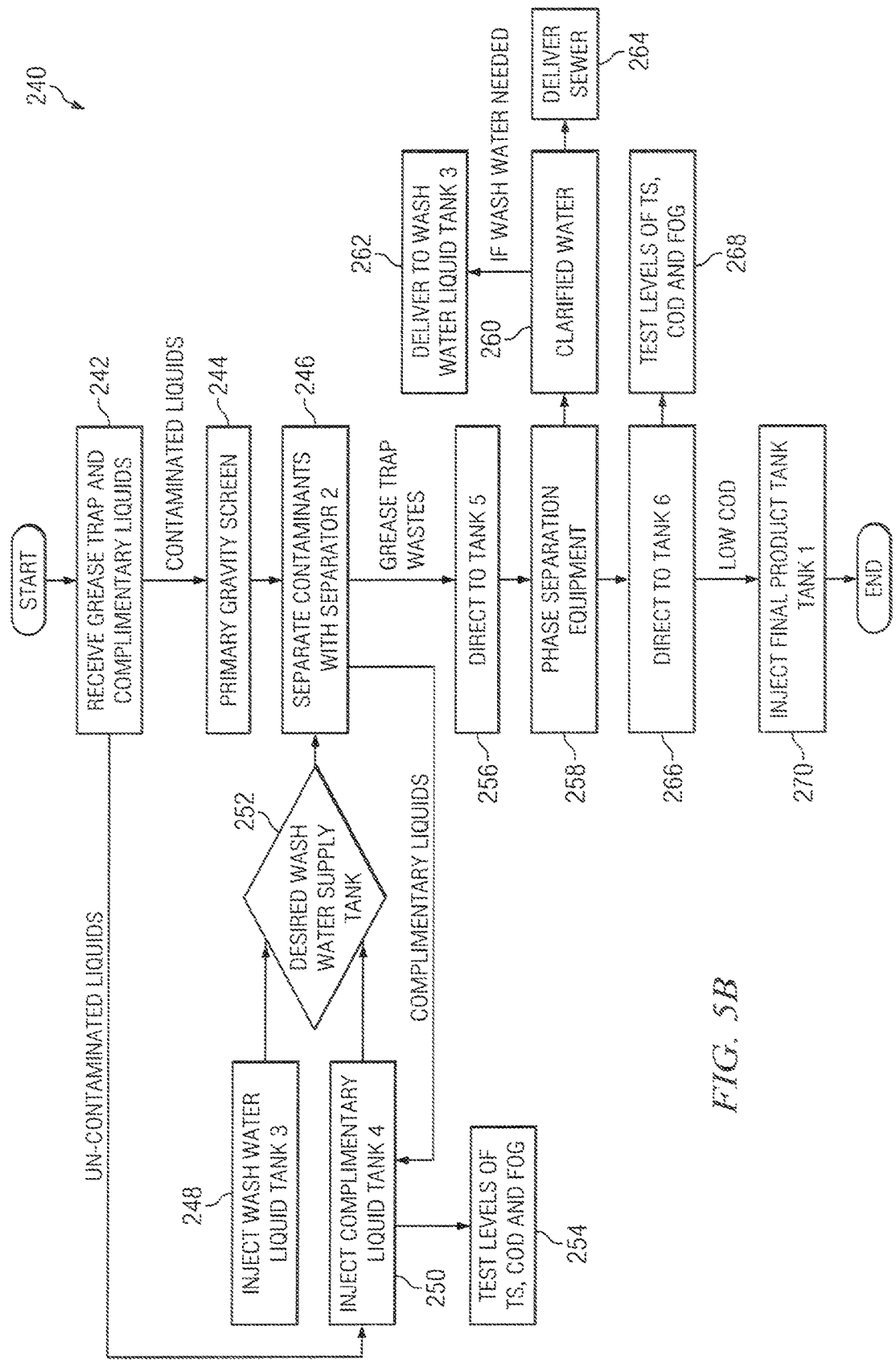
FIG. 5B is a flow chart illustrating FOG processing in accordance with an embodiment of the present invention.

A flow chart 240 illustrating FOG processing in accordance with an embodiment of the present invention is shown in FIG. 5B. At block 242, FOG and/or complimentary liquids are received at a waste processing facility. The FOG and/or complimentary liquids are directed to a primary gravity screen which separates non-digestible contaminates at block 244. A secondary centrifugal separator (Secondary Separator) separates non-digestible contaminates from the complimentary liquids and/or FOG, as indicated at block 246. Such non-digestible contaminates include, without limitation, plastic, glass, ceramics, bones, seeds, cardboard, and the like. At blocks 250 and 248, complimentary liquid from Tank 4 and/or wash water liquid from Tank 3 may be injected into the Secondary Separator, based upon decision block 252.

At block 254, the FOG and/or complimentary liquids are tested for the percentages of (i) total solids (TS), (ii) chemical oxygen demand (COD) and (iii) fats, oils, and greases (FOG) using the same method described above with respect to testing the semi-processed organic slurry.

The complimentary liquids and/or FOG are then pumped out of the secondary separator using pumps into Tank 5 at block 256. For example, the complimentary liquids and/or FOG may be pumped to Tank 1 (164), Tank 4 (168) and/or Tank 5 (150). At block 258, the complimentary liquids and/or FOG are pumped to a FOG Phase-separation unit which separates the FOG from the clarified water. The clarified water is extracted from the Phase-separation equipment, and then either directed to Tank 3 or to the sewer, as indicated at blocks 260, 262 and 264. The FOG is then be pumped into Tank 6 at block 266.

At block 268, the FOG and/or complimentary liquids are again tested for the percentages of (i) total solids (TS), (ii) chemical oxygen demand (COD) and (iii) fats, oils, and greases (FOG) using the same method described above with respect to testing the organic waste. The content of Tank 6 is injected into Tank 1 if the COD is low, at block 270.

Figure 5C:
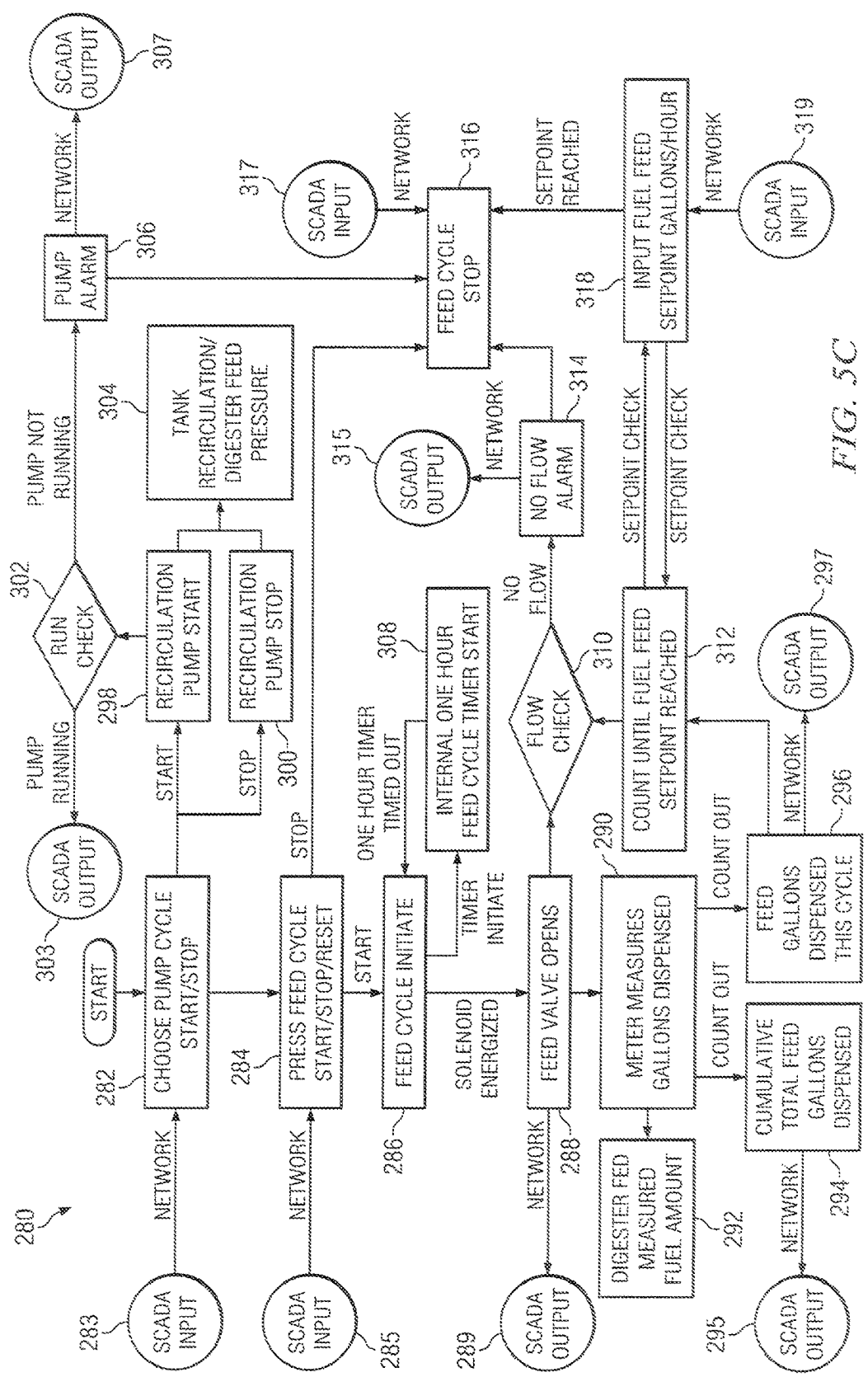
FIG. 5C is a flow chart illustrating anaerobic digester fuel product processing in accordance with an embodiment of the present invention.

A flow chart 280 illustrating anaerobic digester fuel product processing in accordance with an embodiment of the present invention is shown in FIG. 5C. The digester feed system functions are controlled by a programmable logic controller (PLC). The PLC controlled digester feed system communicates with the facility's supervisory control and data acquisition system (SCADA). All functions, setpoints, and alarms programmed into the PLC are available to the facility's control room via a SCADA communications interface. For instance, SCADA input and output is shown at blocks 283, 285, 289, 295, 297, 303, 307, 315, 317 and 319. According to at least one embodiment, the PLC has several control screens that allow for operation of multiple digester feed systems. At block 282, either a pump cycle start or a pump cycle stop is selected. Depending on the selection, the recirculation pump is either started or stopped, as indicated at blocks 298 and 300. If a pump cycle start was selected, then a determination is made as to whether the pump actually started, at decision block 302. If the pump did not start, then a pump alarm is triggered, as indicated at block 306. The tank recirculation and/or digester feed pressures may be determined at block 304.

At block 284, a feed cycle start, a feed cycle stop or a feed cycle reset is selected. Depending on the selection, the feed cycle is either started or stopped, as indicated at blocks 286 and 316. If the feed cycle start was selected, an internal one hour feed cycle time is also started at block 308, and the solenoid is energized and the feed valve is opened at block 288. At decision block 310, a determination is made as to whether there is a flow. If there is no flow then a flow alarm is triggered at block 314. A flow meter measures the amount of uniform fuel product is dispensed, and the gallons of such product is captured, as indicated at block 290 and 292. At blocks 294 and 296, the cumulative total and cycle total of uniform fuel product dispensed is recorded. The meter continues until the appropriate uniform fuel product setpoint is reached at block 312. Once the desired feed amount setpoint is reached as determined at block 318, the PLC closes the feed valve and waits the remainder of the one hour period for the feed cycle to be restarted, as indicated at block 316.

By programmatically controlling the feed valve, the total solids load of the digester is better balanced and the load transients are managed thereby creating a more stable operating environment.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

The present invention thus includes a computer program which may be hosted on a storage medium and includes instructions which perform the processes set forth in the present specification. The storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise then as specifically described.

The invention claimed is:

1. An organic waste processing system to produce a slurry for the production of bio-gas, transportation fuels or chemical products, and a residual solid, comprising:
    a hopper configured to receive organic waste having contaminants including COD from one or more sources;
    a separator system in communication with the hopper and configured to receive the organic waste from the hopper and to remove at least a portion of the contaminants in the organic waste, wherein the separator system comprises a primary separator;
    a wash water liquid tank in communication with the separator system and containing wash water, wherein at least a portion of the wash water from the wash water tank is periodically injected into the separator system upon request;
    a product tank in communication with the separator system and configured to receive organic waste from the separator system, which has been processed by the separator system; and
    a make-up product tank in communication with the separator system and configured to receive the organic waste from the separator system having low COD, wherein at least a portion of the organic waste from the make-up product tank is periodically injected into the product tank upon request.

2. The system of claim 1, including a complementary liquid tank in communication with the separator system and containing complementary liquids, wherein at least a portion of the complementary liquids from the complementary liquid tank is periodically injected into the separator system upon request.

3. The system of claim 2, wherein complementary liquids comprises at least one selected from the group consisting of grease trap material, deceased consumer products, off-spec consumer products, and beverage industry industrial process waste waters.

4. The system of claim 1, including an anaerobic digestor system configured to receive the organic waste from the product tank, wherein the anaerobic digestor system comprises a flow meter, a control valve and an anaerobic digestor tank, wherein the control valve has an open and closed position.

5. The system of claim 4, including a programmable logic controller, wherein the programmable logic controller is configured to periodically inject organic waste into the anaerobic digestor tank to enhance anaerobic digestion, wherein the programmable logic controller is configured to monitor the flow meter and to open and close the control valve to inject the organic waste into the anaerobic digestor tank.

6. The system of claim 5, further comprising a supervisory control and data acquisition interface configured to control at least a portion of the organic waste processing system remotely over the internet.

7. The system of claim 5, wherein the programmable logic controller is configured to control at least one selected from the group consisting of a pump cycle start, a pump cycle stop, a feed cycle start, a feed cycle stop, a feed cycle reset.

8. The system of claim 5, wherein the programmable logic controller is configured to close a control valve, associated with an anaerobic digestor system, after a predetermined setpoint is reached.

9. The system of claim 5, wherein the programmable logic controller is configured to monitor at least one selected from the group consisting of a cumulative amount of the organic waste fed into an anaerobic digestor tank, associated with an anaerobic digestor system, and a current cycle amount of the organic waste fed into the anaerobic digestor tank.

10. The system of claim 1, wherein the primary separator is a centrifugal separator.

11. The system of claim 1, the separator system further comprising a secondary separator in communication with the primary separator and configured to receive the organic waste from the primary centrifugal separator and to remove at least a portion of the contaminants in the organic waste.

12. The system of claim 11, wherein the secondary separator is a centrifugal separator.

13. The system of claim 11, further comprising a FOG tank in communication with the separator system and containing FOG, wherein at least a portion of the FOG from the FOG tank is periodically injected into the product tank upon request.

14. The system of claim 11, further comprising a phase separated FOG tank in communication with the separator system and containing phase separated FOG, wherein at least a portion of the phase separated FOG from the phase separated FOG tank is periodically injected into the product tank upon request.

15. The system of claim 11, the primary separator is configured to remove contaminants greater than 15 millimeters from the organic waste.

16. The system of claim 11, the secondary separator is configured to remove contaminants greater than 8 millimeters from the organic waste.

17. A method for producing, from organic wastes having contaminants, solids, and levels of COD, an organic waste slurry for the production of bio-gas, transportation fuels or chemical products, comprising:
  removing at least a portion of the contaminants from the organic waste to make a first slurry;
  removing at least a portion of the contaminants from the organic waste to make a second slurry;
  providing a supply of FOG liquids; and
  blending into the first slurry some of the second slurry and some of the FOG liquids to produce an organic waste slurry having substantially ten to fifteen percent in total solids measured by weight and having levels of COD measured in mg/L.

18. The method of claim 17, including utilizing a separator system to remove contaminants from the organic wastes to make the first and second slurries, the separator system including a primary separator.

19. The method of claim 18, wherein the primary separator is a centrifugal separator.

20. The method of claim 18, wherein the separator system further includes a secondary separator in communication with the primary separator.

21. The method of claim 20, wherein the secondary separator is a centrifugal separator.

22. The method of claim 18, including providing a supply of wash water, and injecting some of the wash water into the separator system.

23. The method of claim 18, including providing a supply of wash water, and injecting some of the wash water into the first slurry.

24. The method of claim 18, including providing a supply of complementary liquids, and injecting some of the complementary liquids into the separator system.

25. The method of claim 18, including providing a supply of complementary liquids, and injecting some of the complementary liquids into the first slurry.

26. The method of claim 17, wherein the supply of FOG liquids is a supply of raw FOG liquids.

27. The method of claim 17, wherein the supply of FOG liquids is a supply of phase separated FOG liquids.

* * * * *